United States Patent [19]

Eaton et al.

[11] Patent Number: 5,760,266
[45] Date of Patent: Jun. 2, 1998

[54] METHOD FOR THE CYCLOTRIMERIZATION OF ALKYNES IN AQUEOUS SOLUTIONS

[75] Inventors: Bruce Eaton, Boulder, Colo.; Matthew S. Sigman, Pullman, Wash.

[73] Assignee: NeXstar Pharmaceuticals, Inc., Boulder, Colo.

[21] Appl. No.: 816,588

[22] Filed: Mar. 13, 1997

Related U.S. Application Data

[62] Division of Ser. No. 619,228, Mar. 20, 1996, Pat. No. 5,659,069.
[51] Int. Cl.$^6$ ............................. C07F 17/02; C07F 15/00
[52] U.S. Cl. ..................... 556/136; 556/145; 502/152; 526/943
[58] Field of Search ............................... 556/136, 145; 526/943; 502/152

[56] References Cited

U.S. PATENT DOCUMENTS

| | | | |
|---|---|---|---|
| 4,656,299 | 4/1987 | Fujii et al. | 556/22 |
| 4,999,443 | 3/1991 | Bertleff et al. | 556/136 |
| 5,103,065 | 4/1992 | Bertleff et al. | 568/300 |
| 5,284,982 | 2/1994 | Kupper et al. | 568/811 |

OTHER PUBLICATIONS

Arthurs et al., Journal of Organometallic Chemistry, vol. 291, pp. 231–251, 1985.
Divers et al., Journal of Organometallic Chemistry, vol. 447, pp. 291–298, 1993.
Gleiter et al., Organometallics, vol. 12, No. 5, pp. 1889–1889, 1993.
Arthurs et al., Journal of the Chemincal Society, Dalton Transactions, No. 11, pp. 2615–2619, 1987.
Alario et al. (1986) J. Chem. Soc., Chem. Commun. 202.
Amrani et al. (1989) Organometallics 8:542.
Borrini et al. (1985) J. Molecular Catalysis 30:181.
Cash et al. (1973) J. Organometallic Chemistry 50:277.
Collman et al. (1968) Inorg. Chem. 7:1298.
Collman et al. (1987) in *Principles and Applications of Organotransition Metal Chemistry* University Science Books: Mill Valley, CA, pp. 870–879.
Du Plessis et al. (1991) J. Molecular Catalysis 64:269.
Franzus et al. (1959) J. Chem. Soc. 81:1514.
Grigg et al. (1988) J. Chem. Soc. Perkin Trans. I 1357.
Lachmann et al. (1987) J. Molecular Catalysis 42:151.
Lutz (1961) J. Am. Chem. Soc. 83:2551.
Meriwether et al. (1961) J. Org. Chem. 26:5155.
Nagel and Kinzel (1986) Chem. Ber. 119:1731.
Novak and Grubbs (1988) J. Am. Chem. Soc. 110:7542.
Parshall (1980) in *Homogeneous Catalysis;* ch. 11, Wiley: New York.
Reppe et al. (1948) Justus Liebigs Ann. Chem. 560:1.
Rosenthal and Schulz (1987) J. Organometallic Chemistry 321:103.
Schore (1988) Chem. Rev. 88:1081.
Sinou (1987) Bull. Soc. Chim. Fr. 3:480.
Toth and Hanson (1990) Tetrahedron: Asymmetry 1:895.
Vollhardt and Bergman (1974) J. Am. Chem. Soc. 96:4996.
Vollhardt(1984) Angew. Chem. Int. Ed. Engl. 23:539.
Wakatsuki and Yamazaki (1974) J. Organometallic Chemistry 64:393.
Yamazaki and Hagihara (1967) J. Organometallic Chemistry 7:22.

*Primary Examiner*—Porfirio Nazario-Gonzalez
*Attorney, Agent, or Firm*—Swanson & Bratschun, LLC

[57] ABSTRACT

This invention discloses an improved method for the [2+2+2] cyclotrimerization reaction in aqueous solutions using a water soluble transition metal catalyst.

19 Claims, No Drawings

METHOD FOR THE CYCLOTRIMERIZATION OF ALKYNES IN AQUEOUS SOLUTIONS

This application is a divisional of United States application Ser. No. 08/619,228 filed Mar. 20, 1996, now U.S. Pat. No. 5,659,069.

FIELD OF THE INVENTION

This invention relates to the field of synthetic chemistry. Specifically, this invention describes a novel process for [2+2+2] cyclotrimerization reactions in aqueous solutions. Most preferably, the invention includes a process for the [2+2] cyclotrimerization of alkynes to form substituted aromatic compounds. Also included in the invention are novel water soluble transition metal catalysts which are capable of catalyzing [2+2+2] cyclotrimerization reactions in aqueous solutions.

BACKGROUND OF THE INVENTION

Many important medicinal compounds contain achiral aromatic groups with appended chiral substituents. One of the most powerful methods for the construction of products comprising aromatic ring systems (benzenes, naphthalenes, etc.) is cyclopentadienyl cobalt (CpCo) transition metal mediated [2+2+2] cycloaddition of first, second and third reactant alkynes (referred to herein as the "cyclotrimerization" of alkynes). Vollhardt has used this reaction in the eloquent syntheses of many biologically active compounds. (Vollhardt (1984) Angew. Chem. Int. Ed. Engl. 23:539, and references therein). It should be noted that transition metal mediated [2+2+2] cyclotrimerization is not limited to alkyne reactants and that non-aromatic six membered ring products can be assembled by combining alkyne and alkene reactants. Additionally, heterocyclic aromatic ring systems, such as pyridines, can be synthesized by cyclotrimerization of alkynes and nitriles.

The cyclotrimerization of allynes to aromatic compounds is, therefore, of fundamental importance in the area of synthetic chemistry and considerable effort has gone into the development of methods to perform this reaction. (See, e.g., Vollhardt (1984) Angew. Chem. Int. Ed. End 23:539, and references therein; Collman et al. (1987) in *Principles and Applications of Organotransition Metal Chemistry*, University Science Books: Mill Valley, Calif., pp. 870–879; Schore (1988) Chem. Rev. 88:1081).

The thermal cyclotrimerization of acetylene to benzene was first reported by Berthelot in 1866. (Berthelot (1866) C. R. Acad. Sci. 62:905). The reaction required elevated temperatures (400° C.) and gave a mixture of products. In 1949, Reppe et al. described a transition metal mediated version of this transformation, in which nickel was employed as the catalyst. The major product of this reaction, however, was cyclooctatetraene not benzene. (Reppe et al. (1948) Justus Liebics Ann. Chem. 560:1). Several transition metals have now been identified as active catalysts in the [2+2+2] cyclotrimerization of alkynes to aromatic compounds, some of which are described below.

A number of studies have been undertaken using Ziegler type catalysts, such as TiCl$_4$/AlEt$_3$, to perform [2+2+2] cyclotrimerizations. The reactions are carried out in an inert solvent, such as benzene, or absolute ethanol at refluxing temperatures. Generally, only alkyl or phenyl substituents are allowed and the reactions typically produce polymeric side products. (Parshall (1980) in *Homogeneous Catalysis*; ch. 11, Wiley: New York; Franzus et al. (1959) J. Am. Chem. Soc. 81:1514; Meriwether et al. (1961) J. Org. Chem. 26:5155–5163; Lutz (1961) J. Am. Chem. Soc. 83:2551; Lachmann et al. (1987) J. Molecular Catalysis 42:151; Du Plessis et al. (1991) J. Mol. Catal. 64:269). Additionally, Ziegler type catalysts will not survive aqueous conditions.

Several rhodium catalysts, for example catalysts 1a–c and 2a–c, demonstrate the ability to cyclotrimerize alkynes. (See e.g., Collman et al. (1968) Inorg. Chem. 7:1298; Wakatsuki and Yamazaki (1974) J. Organomet. Chem. 50:393; Cash et al. (1973) J. Organomet. Chem. 50:277; Borrini et al. (1985) J. Molecular Catalysis 30:181. See also, Grigg et al. (1988) J. Chem. Soc. Perkin Trans. I 1357–1364, for a discussion of Wilkinson's catalyst [(PPh$_3$RhCl)]). These reactions are run in anhydrous solvents, such as, absolute ethanol and produce many catalytically inactive metal complexes, resulting in low catalyst turnovers. Additionally, rhodium is too expensive to be considered for large scale synthetic use.

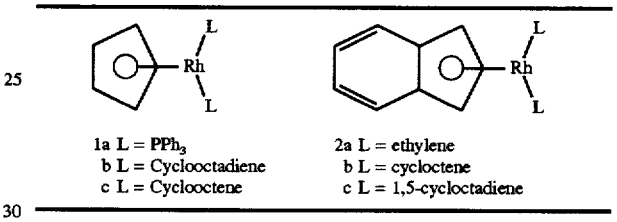

1a L = PPh$_3$
b L = Cyclooctadiene
c L = Cyclooctene

2a L = ethylene
b L = cycloctene
c L = 1,5-cyclooctadiene

As mentioned above, the use of nickel catalysts in the cyclotrimerization of alkynes was first explored in 1948, resulting mostly in cyclooctatetraene formation. (Reppe et al. (1948) Justus Liebics Ann. Chem. 560:1). In more recent studies Ni catalysts 3a–c exhibited good selectivity or cyclotrimerization product, with the formation of no unwanted cyclooctatetraene side products. (Rosenthal and Schulz (1987) J. Organomet. Chem. 321:103).

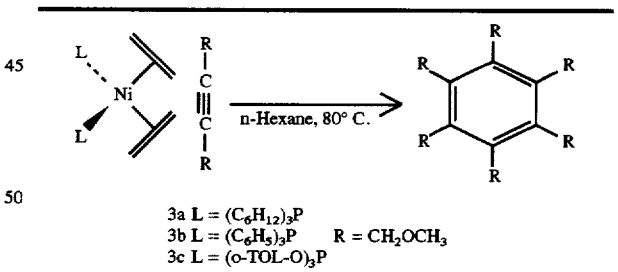

3a L = (C$_6$H$_{12}$)$_3$P
3b L = (C$_6$H$_5$)$_3$P    R = CH$_2$OCH$_3$
3c L = (o-TOL-O)$_3$P

The use of trialkyl phosphines in conjunction with nickel catalyst 4, also gives good yields of cyclic trimer with some dimer formation, but no cyclooctatetraene (Table 1). In the case where no trialkyl phosphine ligands were present, dimer was reported to be the major product with some cyclooctatetraene formation. These results indicate the production of a phosphine-nickel catalyst in situ, followed by cyclotrimerization. The electron donating P(Bu)$_3$ ligand demonstrated the best selectivity to form cyclic trimers. These reactions are run in dry inert solvents at elevated temperatures.

TABLE 1

Trialkyl Phosphine structure (above table):

```
    4
    |
    Ni
    |
    7
    4
```

| Trialkyl Phosphine Co-catalyst (2:1) Ratio | Trimer % | Cyclo-ctatetraene % | Dimer % RC≡C—CH=CHR |
|---|---|---|---|
| none | 1.1 | 9 | 66.3 |
| P(Ph)₃ | 80.8 | 0 | 17 |
| P(Bu)₃ | 83 | 0 | 13 |
| P(Cy)₃ | 75 | 0 | 19 |

By far the most studied and useful cyclotrimerization catalysts have been of the η⁵-cyclopentadienyl cobalt (CpCo) family. In 1967, Yamazaki and Hagihara isolated the first cobalt cyclopentadiene triphenylphosphine complex (CpCoP(Ph)₃), which when treated with a stoichiometric amount of diphenylacetylene in refluxing toluene produced hexaphenylbenzene in 8% yield after one hour. (Yamazaki and Hagihara (1967) J. Organomet. Chem. 7:22). Cobalt cyclopentadiene dicarbonyl (CpCo(CO)₂) (5), a commercially available catalyst, reacts catalytically with bis-alkynes (6) in refluxing n-octane to form several bicyclic systems (7),.. including benzocyclobutenes (n=2) in 45% yield. (Vollhardt and Bergman (1974) J. Am. Chem. Soc 96:4996).

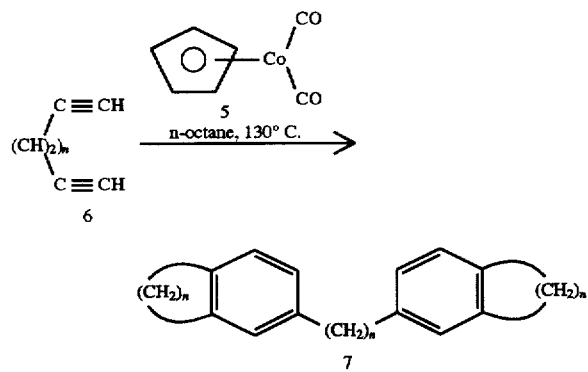

Vollhardt was the first to realize the potential of cobalt catalyzed cyclotrimerization. (Vollhardt and Bergman (1974) J. Am. Chem. Soc. 96:4996; Vollhardt (1984) Angew Chem. Int. Ed. Engl. 23:539) When it appeared that everything had been done in metal-mediated [2+2+2] cyclotrimerization, additional landmark reports appeared that -expanded the repertoire of synthetic transformations. Recent examples that demonstrate the breadth of chemistry and concomitant diversity in structures that may be assembled by cobalt catalyzed cyclotrimeriztion include steroids (Funk and Vollhardt (1980) J. Am. Chem. Soc. 102:5253; Sternberg and Vollhardt (1984) J. Org. Chem. 49:1564; Hillard et al. (1983) Tetrahedron 37:905; Lecker et al. (1986) J. Am. Chem. Soc. 108:856), carbazoles (Grotjahn and Vollhardt (1986) J. Am. Chem. Soc. 108:2091; Boese et al. (1994) Synthesis 1374), stemodin (Germanas et al. (1991) J. Am. Chem. Soc. 113:4006), illudol (Johnson and Vollhardt (1991) J. Am. Chem. Soc. 113:381), phenylenes (Schmidt-Radde and Vollhardt (1992) J. Am. Chem. Soc. 114:9713), γ-lycorane (Grotjahn and Vollhardt (1993) Synthesis 579) and the ergot alkaloids lysergic acid and lysergene (Saá et al. (1994) Synlett., 487). From conducting oligomers to important medicinal compounds, cyclotrimerization has had an enormous impact on the synthetic strategies that can be envisaged.

Until recently, water was considered to be detrimental to low valent organometallic transition metal catalysts,. such as CpCo, due to their sensitivity to both oxygen and water, resulting in either oxidation of the metal or hydrolysis of the organometallic compound. (Parshall (1980) in Homogeneous Catalysis Wiley: New York ). Water has been used as a media for a number of higher oxidation state organometallic-mediated transformations, including polymerization reactions (Novak and Grubbs (1988) J. Am. Chem. Soc. 110:7542–7543), asymmetric hydrogenation of alkynes using water-soluble rhodium complexes of sulfonated tertiary phosphines and water-soluble diphosphines (Toth and Hanson (1990) Tetrahedron: Asymmetry 1:895–912; Nagel and Kinzel (1986) Chem. Ber. 119:1731; Alario et al. (1986) J. Chem. Soc. Chem. Commun. 202–203; Amrani et al. (1989) Organometallics 8:542–547; Sinou (1987) Bull. Soc. Chim. Fr. 480) and asymmetric hydrogenation of imines (Bakos et al. (1989) Abstract of 5th OMCOS, Florence. Italy, PS1-36). These reactions exhibit increased selectivity in product distribution and increased activity of catalysts. In addition, the separation of organic products in aqueous solutions from the water soluble catalysts has enhanced product recovery and enabled the recovery and reuse of the catalyst. (Novak and Grubbs (1988) J. Am. Chem. Soc. 110:7542–7543; Toth and Hanson (1990) Tetrahedron: Asymmetry 1:895–912; Nagel and Kinzel (1986) Chem. Ber. 119:1731; Alario et al. (1986) J. Chem. Soc. Chem. Commun. 202–203; Amrani et al. (1989) Organometallics 8:542–547; Sinou (1987) Bull. Soc. Chim. Fr. 480). Thus, the use of aqueous media has significantly improved these catalytic systems.

Due to environmental and health concerns, and the costs associated with the use and disposal of organic solvents, there is a great deal of interest in developing reactions that can be performed in aqueous solutions. For all of these reasons it would, therefore, be desirable to be able to perform organometallic-mediated reactions involving low valent metals in aqueous solutions. In order to perform organometallic reactions in aqueous media, however, it is first necessary to prepare water soluble catalysts. To date there have been no reports of low valent transition metal catalysts useful for cyclotrimerization reactions that are stable and soluble in water.

BRIEF SUMMARY OF THE INVENTION

The present invention includes a novel method for performing [2+2+2] cyclotrimerization reactions in aqueous solutions. A preferred embodiment of this invention utilizes a novel water soluble cobalt catalyst. Included in the present invention is a method for the preparation of a cobalt catalyst which is both soluble and stable in aqueous solutions. The novel catalyst so produced is also part of this invention.

This invention includes a reaction scheme for producing a wide variety of substituted aromatic compounds. A key element in the production of these compounds is the use of a novel low valent organometallic catalyst that is both soluble and stable in aqueous solutions. In a preferred embodiment the metal is cobalt (I). The utilization of the novel cobalt catalysts of this invention results in increased yields, rates, selectivity and also tolerates a wider array of functional groups over the catalysts of the prior art. Additionally, the use of aqueous media enables the recovery and reuse of the catalyst and allows the reactions to be run in a much safer and more economical manner.

The aromatic compounds of the invention have many uses, particularly in the area of engineering resins, pharmaceuticals, diagnostics and combinatorial chemistry applications, such as those disclosed in United States patent application Ser. No. 08/309,245, filed Sep. 20, 1994, entitled "Parallel SELEX", which is herein specifically incorporated by reference. Any use where a cyclic chemical product, particularly those containing a six membered ring, could be desirable is within the scope of this invention. Applications of the products of this invention include various therapeutic, prophylactic, diagnostic and cosmetic uses. Specific classes of medical conditions that may be treated by products of the present invention include, but are not limited to inflammation, cardiovascular disorders, neoplastic conditions, metabolic disorders, parasitic diseases and infectious diseases. More specifically, the products of the invention may be useful in treating or preventing cancer, angina, arthritis, asthma, allergies, rhinitis, shock, inflammatory bowel disease, low blood pressure and systemic treatment of pain and inflammation, local trauma such as wounds, burns and rashes. The desirable products can be administered by any method known to one of ordinary skill in the art.

Additionally, the desirable products of this invention may find use as agricultural agents. Specifically, the desirable products can be herbicides, pesticides, growth regulators, etc. The use and administration of the products of this invention for agricultural purposes is known by one of ordinary skill in the art. The products of the invention can also be used in chemical manufacturing processes.

The desirable products of this invention can also find use in the area of engineering resins, for example, as monomers in polymeric resins, such as, "KEVLAR®" and "TORLON®", which are aromatic polyamide fibers.

Finally, the desirable products of this invention can find use as metal chelators to extract metals from solution.

The method of this invention is not limited to [2+2+2] cyclotrimerizations of alkynes to produce substituted aromatic compounds, but is compatible with other [2+2+2] coupling reactions to produce non-aromatic six membered ring systems and heterocyclic aromatic ring systems.

DETAILED DESCRIPTION OF THE INVENTION

The present invention includes a method for performing [2+2+2] cyclotrimerization reactions in aqueous media. In a preferred embodiment of the present invention a novel water soluble cobalt catalyst is utilized to effect the [2+2+2] cyclotrimerization of alkynes in aqueous media to produce a wide variety of substituted aromatic compounds. The method of the present invention can be extended to the production of non-aromatic six membered ring systems and aromatic heterocyclic compounds.

The present invention extends to all novel compounds that can be prepared according to the methods of the present invention.

Included in the present invention is a method for the preparation of a transition metal catalyst for [2+2+2] cyclotrimerization reactions which is both soluble and stable in aqueous solutions. In a preferred embodiment the transition metal catalyst is a cobalt (I) catalyst. The improved catalyst achieves improved yields, increased rates, improved selectivity of product distribution and allows for the synthesis of aromatic compounds that would be difficult to prepare by other methods. The use of aqueous media facilitates the recovery and reuse of catalyst. The novel catalyst so produced is also part of this invention.

Illustrative substituted aromatic compounds produced by the method of this invention are shown in Table 2. Table 2 represents only a partial list of the substituted aromatic compounds that may be produced according to the method of this invention.

Certain terms used to describe the invention herein are defined as follows:

"Cyclotrimerization" means a reaction in which molecules are joined together to form cyclic compounds. A "[2+2+2] cyclotrimerization" is a reaction in which three unsaturated moieties, preferably alkynes, are joined together to form a six numbered ring, such as benzene, a substituted benzene, or fused aromatic ring systems, such as naphthalene and indole. Included within this definition are intermolecular reactions of a single alkyne $R_1C{\equiv}CR_2$, intermolecular reactions between 2 or 3 different alkynes, and partially intramolecular reactions between a diyne and an alkyne $R_1C{\equiv}CR_2$ or a diyne and an alkyne. Also specifically included within this definition are reactions that form non-aromatic six membered rings and heterocyclic aromatic compounds, such as a pyridine or a substituted pyridine.

The "catalyst" of the present invention is most generally defined as a water soluble transition metal complex, which is capable of enhancing the rate of [2+2+2] cyclotrimerization reactions of unsaturated moieties to produce six membered rings. In the preferred embodiment the transition metal is cobalt and the compounds formed are substituted aromatic compounds. The catalyst will be defined in more detail below.

The general reaction of one embodiment of the present invention can be characterized as follows:

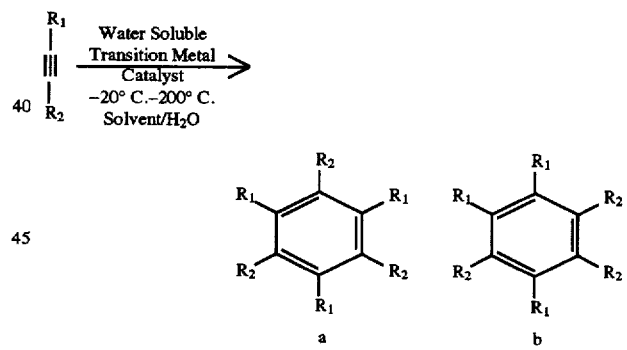

$R_1$ and $R_2$ can be independently selected from a wide variety of functional groups, including but not limited to hydrogen, alcohols (1°, 2° and 3°), ethers, ketones, esters, amides (1° and 2°), amines (1° and 2°), sulfides, sulfates, phosphates, C1–C20 alkanes, substituted C1–C20 alkanes, halogens, thioethers, thioesters, etc. In contrast to known CpCo or conventional methods, it is generally unnecessary to protect any of the functional groups present within $R_1$ and $R_2$, such as alcohols. Additionally, it is not necessary that alkyne $R_1C{\equiv}CR_2$ be water soluble, so long as it is at least emulsified.

More specifically $R_1$ and $R_2$ can be independently selected from the group consisting of H, C1–C5 alcohols (1°, 2° and 3°), C1–C5 amines (1° and 2°), C1–C5 esters or C1–C5 ketones.

In one embodiment of the present invention, $R_1$ and $R_2$ are independently selected from the group consisting of: H, —CH$_2$OH, —COCH$_3$, —CO$_2$CH$_3$, (CH$_2$)$_2$OH, —CH$_2$NH(CH$_3$), —C(CH$_3$)$_2$OH and —CH$_2$N(CH$_3$)$_2$.

Table 2 delineates a partial list of the substituted aromatic compounds that can be produced according to the method of this invention. As can be seen in Table 2, substituted aromatic compounds can be produced that contain a wide range of functional groups, including but not limited to: alcohols, ethers, ketones, esters, amides, amines, sulfides, sulfates, phosphates, C1–C20 alkanes, halogens, such as, chlorine and fluorine, thioethers and thioesters. The inventors hereto believe that compounds 13–18 are novel compounds.

A notable application for the aromatic alcohols and amines of this invention is the area of engineering resins. Compounds such as these are used in the synthesis of a number of polymers containing aromatic rings, an example of which is KEVLAR®, an aromatic polyamide fiber used in the synthesis of many products. Currently, the synthesis of these compounds requires relatively harsh conditions. Using the method of this invention, these compounds can be synthesized under mild conditions with a simplified purification procedure yielding a significantly more economical process. The synthesis conditions of this invention are also compatible with conditions for nucleic acid facilitated product formation as described in United States patent application Ser. No. 08/309,245, filed Sep. 20, 1994, entitled "Parallel SELEX".

TABLE 2

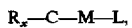

| R$_1$ | R$_2$ | Yield, % | a/b | Compound |
|---|---|---|---|---|
| —CH$_2$OH | —CH$_2$OH | 52 | — | 12 |
| H | —COCH$_3$ | 66 | 67/33[1] | 13 |
| H | —CO$_2$CH$_3$ | 67 | 30/70 | 14 |
| H | (CH$_2$)$_2$OH | 68 | 27/73[2] | 15 |
| H | —CH$_2$NH(CH$_3$) | 40 | 35/65[2] | 16 |
| H | —C(CH$_3$)$_2$OH | 57 | 35/65 | 17 |
| H | —CH$_2$N(CH$_3$)$_2$ | 78 | 34/66 | 18 |

[1]Minor product not identified as 1, 2, 4 product.
[2]Ratios determined by NMR.

As can be seen in Table 2, the product of the reaction of monosubstituted alkynes, is a 2:1 mixture of the 1, 2, 4 and 1, 3, 5 isomers. The products of the reaction generally precipitate out of the reaction mixture and are easily removed by filtration. The isomers may then be separated by fractional crystallization. The catalyst, which remains soluble in the aqueous solution, can then be reused.

A key element in the method of this invention is the preparation and use of a transition metal catalyst that is both stable and soluble in water. The catalyst of the present invention may be characterized most generally by the following formula:

R$_x$—C—M—L, where C is cyclopentadienyl or indenyl. R is an electron withdrawing group which is attached to C. R may be selected from the group consisting of a nitrile, ester, ketone, amide, chloro or fluoro. X is 0, 1 or 2. An electron withdrawing group is generally necessary at this position in order to solubilize the catalyst. As the number of electron withdrawing groups (R) is increased, the catalyst becomes more reactive, but also less stable resulting in reduced catalyst turnover. It should be noted that the cyclopentadienyl or indenyl ring may contain more than one R group as illustrated below, (Catalyst B). In one embodiment of the present invention, R also contains a highly polar functional group selected from the group consisting of an amine, amide, sulfoxide, sulfonate, hydroxyl, guanidinium, polyamine, putracene, or spermadine. The polar functional group serves to increase the solubility of the catalyst. M is a transition metal selected from the group consisting of Co, Rh, or Ir. In a preferred embodiment of this invention M is cobalt (I). L can be either two separate 2 electron π-ligands or one 4 electron π-ligand. The various ligands that may be employed would be recognized by one of ordinary skill in the art. Examples of common 2 electron π-ligands (L) include, but are not limited to ethylenes, propenes, butenes, pentenes, cyclopentenes, hexenes and cyclohexenes. Examples of common 4 electron π-ligands are cyclobutadiene, cyclohexadiene, or cyclooctadiene. In the preferred embodiment C is cyclopentadienyl, L is cyclooctadiene, x=1 and the catalyst has the following structure:

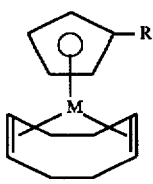

In yet another embodiment of the present invention L may also contain one or more polar functional groups, (R$_3$) selected from the group consisting of an amine, sulfonate, hydroxyl, guanidinium, polyamine, putracene, or spermadine. In one embodiment in which L contains one polar functional group the catalyst has the following structure:

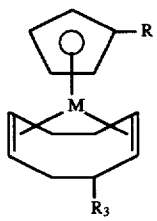

In a second embodiment in which L contains one polar functional group the catalyst has the following structure:

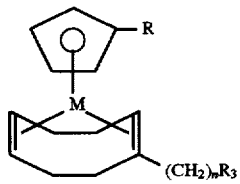

wherein n=1 to 8 and R$_3$ is as defined above.

In yet another embodiment of the present invention the cyclopentyldienyl group can be replaced by an indenyl group, in which case the catalyst would have the following structure for the case in which x=1:

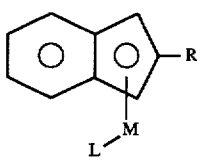

All other groups are the same as provided above for the cyclopentadienyl catalyst.

To illustrate the method of this invention two separate water soluble cobalt catalysts: Catalyst A and Catalyst B were prepared as described in Examples 1 and 2 (Scheme 1 and 2).

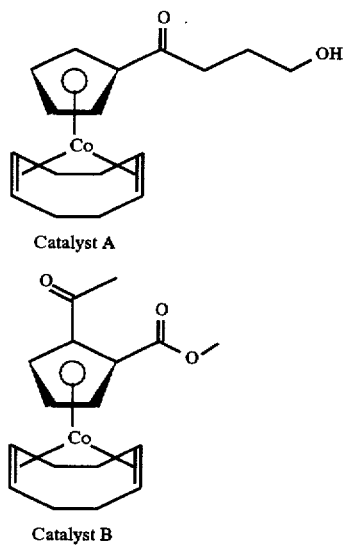

Catalyst A

Catalyst B

Catalyst A contains a ketone as the electron withdrawing group (R). Catalyst B has two electron withdrawing, groups (R), an ester and a ketone, which makes Catalyst B much more reactive than Catalyst A. Catalyst A also contains a polar hydroxyl group, which increases its solubility in water. The reactions illustrated in Table 2 were performed using Catalyst A.

A general reaction scheme for the [2+2+2] cyclotrimerization of alkynes according to the method of this invention is described in Example 3 (Scheme 3). The reaction can be conducted between the temperatures of −20° to 200° C. The preferred temperature range is between 50° and 130° C. In the most preferred embodiment the reaction is conducted at about 85° C. In a preferred embodiment the reaction is conducted in 20–100% of a mixture of an alkyl alcohol, such as methanol or ethanol and water. In the most preferred embodiment the reaction is run in 20%–40 % alcohol/water. Other acceptable solvents include, but are not limited to N, N-dimethyl formamide (DMF)/$H_2O$, tetrahydrofuran (THF) /$H_2O$, and dioxane/$H_2O$.

As stated above, the substituted aromatic compounds produced by the method of this invention are contemplated for use as pharmaceuticals, diagnostic agents, agricultural agents, and in chemical manufacturing processes.

EXAMPLES

The following examples are illustrative of preferred embodiments of the methods of preparation and the products of the invention and are not to be construed as limiting the invention thereto.

General.

All reactions and manipulations were conducted under a dry argon atmosphere using either an inert atmosphere glove-box or standard Schlenck techniques. The $^1H$ and $^{13}C$ NMR spectra were obtained in $CDCl_3$, $C_6D_6$, $D_2O$, $CD_3CN$ or $CH_3OD$ on a Bruker ARX (300 MHz $^1H$) or Bruker AMX (300 MHz $^1H$). IR spectra were recorded on a Perkin-Elmer 1600 Fourier Transform, Infrared (FTIR) Spectrometer. Mass spectral data were obtained from the departmental facility at Washington State University and University of California Berkeley Mass Spectral facilities. Elemental analysis was obtained from Desert Analytics, Tucson, Ariz. Melting points were recorded on a Mel-Temp apparatus and are uncorrected.

Materials.

Alkynes were purchased from Aldrich Chemical Company (Milwaukee, Wis.) or Farchan Chemicals and were either vacuum distilled or recrystallized before use. Chlorotris(triphenylphosphine)cobalt ($Cl[Co(PPh_3)_3]$) was prepared according to the method of Wakatsuki and Yamazaki (1989) Inorg. Synth. 26,189. Sodium methoxycarbonylcyclopentadienide was prepared according to the method of Hart et al. (1980) J. Am. Chem. Soc. 102:1196). ($\eta^5$-methoxycarbonylcyclopentadienyl)-cobalt($\eta^4$-1,5-cyclooctadiene) was prepared according to the method of Wakatsuki and Yamazaki (1985) Bull. Chem. Soc. Jpn. 58:2715. Tetrakis(triphenylphosphite)nickel was prepared according to the method of Levison and Robinson (1971) Inorg. Syn. 13:105.

Example 1

Preparation of Cyclotrimerization Catalyst A

Cyclotrimerization Catalyst A was synthesized from cyclopentadiene as illustrated in Scheme 1. Briefly, sodium cyclopentadienylide was first reacted with butyrolactone in refluxing THF, followed by reaction with chlorotris (triphenylphosphine)cobalt and cyclooctadiene to yield Catalyst A.

SCHEME 1

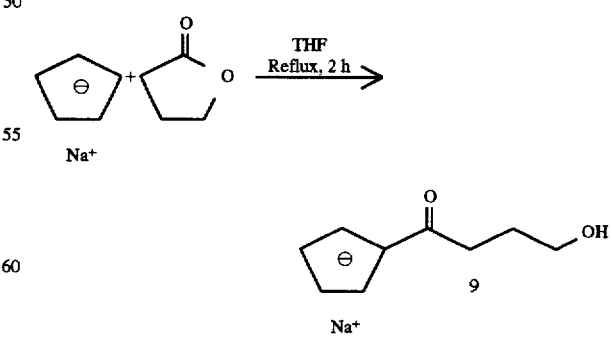

-continued
SCHEME 1

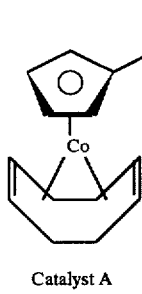

Catalyst A

Preparation of Sodium-buta-4-ol-1-one-cyclopentadienylide (9).

To a flame dried flask containing sodium cyclopentadienylide (10 mmol) freshly prepared in 10 mL of THF, a solution of butyrolactone, 753 μL (9.8 mmol) in 15 mL of THF (freshly distilled from K/benzophenone) was cannulated dropwise over a period of 10 minutes. After 1 hour at room temperature, the reaction vessel was equipped with a reflux condenser and the mixture was heated at reflux for 2 hours. The reaction turned a slightly orange color. After cooling to ambient temperature, the solution was filtered through a medium glass frit and the filtrate was concentrated to approximately 10 mL. The reaction mixture was then added dropwise to a rapidly stirring solution of hexanes (300 mL, sparged) to form a slightly pink powder. The powder was collected by filtration, washed with hexanes (2×30 mL), and dried on a vacuum line to yield 1.236 g (72%) of a white powder. $^1$H NMR (300 MHz, D$_2$O) δ 1.89 (pent, J=7.0), 2.71 (t, J=7.0 Hz, 2H), 3.65 (t, J=7.0 Hz, 2H), 6.20 (m, 2H), 6.67 (m, 2H); $^{13}$C NMR (75 MHz, CD$_3$OD) δ 30.36, 34.10, 61.71, 1 12.95, 115.94, 117.46, 117.85, 122.59, 190.96.

Preparation of Cyclotrimerization Catalyst A.

Toluene (10 mL, freshly distilled from sodium) and cyclooctadiene (10 mL, 81 mmol) were added to a flask and freeze-pumped-thawed (3 cycles). The flask was then charged with 5.0 g, (5.67 mmol) chlorotris (triphenylphosphine)cobalt and stirred vigorously. A solution of 9 (1.41 g, 8.10 mmol) in 10 mL of THF was then added. The solution immediately turned red. After stirring at ambient temperature for 12 hours the reaction mixture was applied to a pad (2 mm×20 mm) of neutral alumina (deactivated with 5% H$_2$O ) and eluted with 10 mL of THF. The eluent was concentrated in vacuo to 3 mL and applied to a column of neutral alumina (2 mm×75 mm). A brown band was first eluted with hexanes, after which, the column was washed with 20% THF/hexanes (50 mL), 50% THF/hexanes (50 mL) and finally THF (50 mL) to elute an orange band which was collected. The solvent was removed in vacuo and the resulting orange solid was dissolved in 0.5 mL of THF and 10 mL of hexanes and placed in a freezer at −30° C. Dark orange crystals were isolated and washed with hexanes to yield 900 mg (50%) of cyclotrimerization Catalyst A; mp 55°–56° C.; $^1$H NMR (300 MHz, CD$_3$CN) δ 1.65 (m, 4H), 2.03 (t, J=6.9 Hz, 2H), 2.36 (m, 4H), 2.84 (t, J=5.3 Hz, 1H), 3.14 (t, J=7.2 Hz, 2H), 3.56 (m, 4H), 3.68 (q, J=6.1 Hz, 2H), 4.24 (t, J=2.1 Hz, 2H), 5.25 (t, J=2.1 Hz, 2H); $^{13}$C NMR (75 MHz, C$_6$D$_6$) δ 28.30, 32.28, 36.75, 62.83, 69.01, 83.37, 88.84, 97.68, 197.26; MS m/z (M$^+$) 318.

Example 2
Preparation of Cyclotrimerization Catalyst B

Cyclotrimerization Catalyst B was synthesized from sodium methoxycarbonylcyclopentadienide as illustrated in Scheme 2. Briefly, sodium methoxycyclopentadienide was first reacted with acetic anhydride in refluxing, THF, followed by reaction with tert-butoxide to form compound 11. Compound 11 was then reacted with chlorotris (triphenylphosphine)cobalt and cyclooctadiene to yield Catalyst B.

SCHEME 2

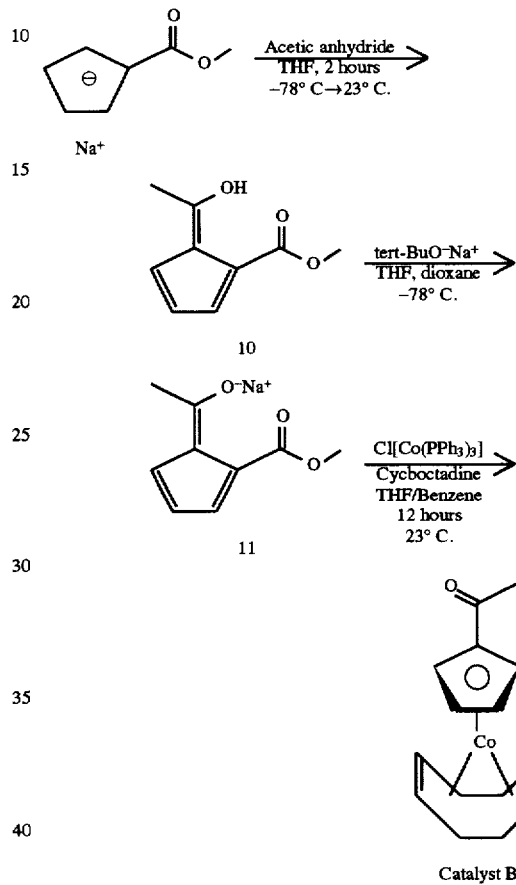

Catalyst B

Preparation of Compound (10).

Sodium methoxycarbonylcyclopentadienide, 1.5 g (10.3 mmol) and 50 mL of freshly distilled TH (from K/benzophenone) were added to a flask and cooled to −78° C. and stirred. A solution of freshly distilled acetic anhydride, 1.15 g (11.3 mmol) and THF (15 mL) was prepared and cannulated slowly into the stirring mixture. Fifteen minutes after addition, the cooling bath was removed and the reaction was allowed to warm to room temperature and stirred for 12 hours. After 12 hours the resulting orange/yellow mixture was dissolved in 200 mL ethyl acetate and washed with brine (5×40 mL). The organic layer was collected and the solvent reduced by rotary evaporation. The resulting yellow oil was subjected to column chromatography (5% EtOAc/hexanes) to yield 694 mg (41%) of a pale yellow solid, compound 10, which was recrystallized from hexanes; mp 58.5°–59.0° C.; $^1$H NMR (300 MHz, CDCl$_3$) δ 2.48 (s, 3H), 3.89 (s, 3H), 6.31 (dd, J=3.1 Hz, 4.6 Hz, 1H), 7.03 (dd, J=1.9 Hz, 4.6 Hz, 1H), 7.37 (dd, J=1.9 Hz, 3.1 Hz, 1H), 15.61 (s, 1H); $^{13}$C NMR (75 MHz, CDCl$_3$) δ 21.10, 52.56, 117.38, 119.40, 121.31, 131.77, 136.68, 169.91, 177.03.

Preparation of Compound (11).

Compound 10, 170 mg (1.023 mmol) was added to a 100 mL flask containing 35 mL of freshly distilled THF and cooled to −78° C. A solution of sodium t-butoxide, 96 mg (1 mmol) and 15 mL of THF was prepared and cannulated into the solution of compound 10. The flask containing the sodium t-butoxide was washed with 8 mL of dioxane, which was also cannulated into the reaction mixture. The reaction was allowed to warm to ambient temperature over 1 hour and stirred for an additional 1.5 hours. The solvent was removed in vacuo and the resulting solid was washed with hexanes (5 mL), toluene (5 mL) and finally hexanes (5 mL) to yield 108 mg of a pale yellow solid compound 11 (57%), which was used without further purification.

Preparation of ($\eta^5$-1-methoxycarbonyl-2-acetylcyclopentadienyl)cobalt ($\eta^4$-cyclooctadiene) (Catalyst B).

To a degassed solution of chlorotris(triphenylphosphine) cobalt, 400 mg (0.451 mmol), cyclooctadiene, 172 μL (1.41 mmol) and 3 mL of freshly distilled toluene (from Na/benzophenone) in a glass bomb, s added a solution of compound 10, 106 mg (0.563 mmol) and 2 mL of freshly distilled THF, upon which the reaction immediately turned red. After stirring at room temperature for 12 hours the reaction mixture was applied to a pad (2 mm×20 mm) of neutral alumina (deactivated with 5% $H_2O$) and eluted with 10 mL of THF. The eluent was concentrated in vacuo to approximately 2 mL and applied to a column of neutral alumina (2 mm×75 mm). The column was washed successively with hexanes eluting a small brown band, toluene eluting 5 a green band and finally 5% THF/toluene eluting a red/orange band which was collected. The solvent was removed in vacuo and the resulting red solid was recrystallized from THF/hexanes to yield 60 mg (40%) of a red solid (cyclotrimerization Catalyst B); mp 95.0°–96.5° C.; $^1$H NMR (300 MHz, $C_6D_6$) δ 1.49 (m, 4H), 2.27 (m, 4H), 2.74 (s, 3H), 3.40 (s, 3H), 3.52 (m, 4H), 4.47 (t, J=2.5 Hz, 1H), 4.75 (pent, J=2.5Hz, 2H); $^{13}$C NMR (75 MHz, $C_6D_6$) δ 31.02, 31.72, 32.11, 51.61, 70.33, 70.46, 86.02, 87.97, 88.29, 90.50, 97.68, 167.10, 196.30; MS m/z ($M^+$) 332.

Example 3
General Procedure for Cobalt Catalyzed Cyclotrimerization Reactions.

Compounds 12–18 (Table 2) were prepared by the following general procedure.

To a glass bomb equipped with a teflon stopcock and stir bar was added 4.5 mmol of an alkyne, 2.5 mol % (112 μmol, 20 mM) of the cobalt catalyst, 3.4 mL of millipore $H_2O$ (sparged with argon) and 2.2 mL of freshly distilled methanol (sparged with argon). The mixture was freeze-pump-thawed for four cycles, placed into a 85° C. oil bath and stirred for 40 hours and cooled to room temperature.

Compound 12.

The bomb was cooled to ambient temperature and the solid precipitate was collected by filtration. The solid was washed with water, THF and collected to give 52% yield of a white solid. $^1$H NMR (300 MHz: $CD_3OD/D_2O$) δ 5.22; $^{13}C(^1H)$ (75 MHz, $CD_3OD$) δ58.92, 140.68; MS m/z ($M^+$) 259.

Compound 13.

Upon cooling to room temperature, the aqueous mixture was extracted with ethyl acetate (3×30 mL). The resulting extract was washed with brine (50 mL) and dried over magnesium sulfate. The solvent was removed in vacuo and the resulting residue was purified by flash chromatography on silica gel using a mixture of acetone (20% ), benzene (20%) and hexanes (60%). Two fractions were collected and characterized.

Compound 13a:

43% of a white solid; $^1$H NMR (300 MHz, $CDCl_3$) δ 2.65 (s, 9H), 8.63 (s, 3H); $^{13}$C NMR (75 MHz, $CDCl_3$) δ 26.74, 131.64, 137.81, 196.54; MS m/z ($M^+$) 204.

Compound 14.

Upon cooling to room ambient temperature and the aqueous mixture was extracted with ethyl acetate (3×25 mL) and the resulting extract was washed with brine (50 mL). The solvent was reduced in vacuo and the resulting residue was purified by flash chromatography on silica gel using a mixture of 25% ethyl acetate in hexanes. Two fractions were collected and characterized.

Compound 14a:

20% of a white solid; $^1$H NMR (300 MHz, $CDCl_3$) δ 3.95 (s, 9H), 8.82 (s, 3H); $^{13}$C NMR (75 MHz, $CDCl_3$) δ 52.59, 131.18, 134.55, 165.38; MS m/z (($M^+$) 252.

Compound 14b:

47% of a clear oil; $^1$H NMR (300 MHz, $CDCl_3$) δ 3.88 (s, 6H), 3.90 (s, 3H), 7.69 (d, J=8.0 Hz, 1H), 8.14 (dd, J=1.6, 8.0 Hz, 1H), 8.36 (d, J=1.6 Hz, 1H); $^{13}$C NMR (75 MHz, $CDCl_3$) δ 52.52, 52.74, 52.81, 128.79, 130.16, 131.53, 132.16, 132.35, 136.13, 165.25, 166.71, 167.48; MS m/z ($M^+$) 252.

Compound 15.

After cooling to ambient temperature, the aqueous mixture was taken up in brine (10 mL) and extracted with ethyl acetate (5×30 mL). The extract was dried over magnesium sulfate and the solvent removed in vacuo. The resulting residue was purified by flash chromatography on silica gel using, 8% methanol in ethyl acetate. One fraction was collected. The fraction yielded 250 mg (68%) of a viscous oil which was identified as a mixture of isomers 15a and 15b (27:73) by NMR. $^1$H NMR (300 MHz, $CD_3OD$) δ $^{13}$C NMR (75 MHz, $CDCl_3$) δ 36.53, 36.90, 39.75, 40.08, 63.90, 64.02, 64.17, 64.29, 128.08, 128.60, 131.05, 131.67, 135.89, 138.03, 138.20, 140.25; MS m/ ($M^+$) 210.

The following alternate procedure was used to separate compounds 15a and 15b. After cooling to ambient temperature, the aqueous mixture was taken up in 3 mL of 25% HCL and washed with methylene chloride (30 mL). The aqueous layer was then made basic using 3M NaOH and was extracted with methylene chloride (3×30 mL). The resulting extract was dried over sodium sulfate and the solvent removed in vacuo to give a clear oil. The two isomers were separated on a column of neutral alumina (deactivated with 5% $H_2O$) eluting, with 5% methanol/2% triethylamine/acetonitrile.

Compound 15a:

27% of a white solid; $^1$H NMR (300 MHz, $CD_3OD$) δ 2.36 (s, 18H), 3.70 (s, 6H), 7.31 (s, 3H); $^{13}$C NMR (75 MHz, $CD_3OD$) δ 45.58, 63.55, 132.73, 137.43.

Compound 15b:

51% of a clear oil: $^1$NMR (300 MHz, $CD_3OD$) δ 2.13 (s, 6H), 2.42 (s, 6H), 2.43 (s, 6H), 3.42 (s, 2H), 3.88 (s, 2H), 3.90 (s, 2H), 7.30 (m, 3H); $^{13}$C NMR (75 MHz, $CD_3OD$) δ 43.14, 43.24, 45.23, 61.50, 61.86, 62.22, 63.97, 131.92, 133.61, 134.64, 135.10, 136.20, 140.68.

Compound 16.

After cooling to ambient temperature the aqueous mixture was taken up in 3 ml 25% HCL and washed with methylene chloride (30 ml). The aqueous layer was then made basic with 3M NaOH and extracted with methylene chloride (3×30 ml). The resulting extract was dried over sodium sulfate and the solvent removed in-vacuo to give a clear oil which was identified as a mixture of isomers. $^{13}C[^1H]$ (75 MHz, $CD_3OD$) δ 33.44, 33.55, 34.92, 35.11, 35.35, 41.61, 53.49, 53.86, 55.23, 55.38, 55.54, 61.47, 61.71, 128.81, 129.55, 130.36, 130.98, 131.15, 132.93, 132.99, 135.96, 137.22, 137.89, 139.60, 139.74, 140.48, 140.95; MS m/z ($M^+$—$NH_2CH_3$) 176.

Compound 17.

After cooling to ambient temperature, the aqueous mixture was taken up in 10 mL of brine and extracted with ethyl acetate (5×30 mL). The extract was dried over magnesium sulfate and the solvent removed in vacuo. The resulting residue was purified by flash chromatography on silica gel using 40% acetone/hexanes. Two fractions were collected.
Compound 17a:

20% of a white solid; $^1$H NMR (300 MHz, CD$_3$OD) δ 1.43 (s, 6H), 7.38 (s, 1H); $^{13}$C NMR (75 MHz, CD$_3$OD) δ 32.11, 73.32, 119.99, 150.18.

Compound 17b:

37% of a white solid; $^1$H NMR (300 MHz, CD$_3$OD) δ 1.40 (s, 6H), 1.55 (s, 6H), 1.57 (s, 6H), 7.12 (dd, J=8.4, 2.1 Hz, 1H), 7.19 (d, J=8.4 Hz, 1H), 7.40 (d, J=2.1 Hz, 1H); $^3$C NMR (75 MHz, CD$_3$OD) δ 31.90, 33.90, 33.92, 72.16, 75.19, 75.59, 123.54, 125.34, 129.01, 144.90, 146.57, 148.31.

Compound 18.

The bomb was cooled to ambient temperature and the aqueous mixture was taken up in 3 ml 25% HCL and washed with methylene chloride (3×30 ml). The aqueous layer was then made basic with 3M NaOH and then extracted three times with methylene chloride (30 ml). The resulting extract was dried over sodium sulfate and the solvent removed in-vacuo to give a clear oil. The two isomers were separated by neutral alumina (deactivated with 5% H$_2$O) eluting with 5% CH$_3$OH/2% triethylamine/Acetonitrile.

(a): 27% of a white solid; $^1$H NMR (300 MHz: CD$_3$OD) δ 2.36 (s, 18H), 3.70 (s, 6H), 7.31 (s, 3H); $^{13}$C($^1$H) (75 MHz, CD$_3$OD) δ 45.58, 63.55, 132.73, 137.43; MS m/(M$^+$) 249.

(b): 51% of a clear oil; $^1$H NMR (300 MHz: CD$_3$OD) δ 2.13 (s, 6H), 2.42 (s, 6H), 2.43 (s, 6H), 3.42 (s, 2H), 3.88 (s, 2H), 3.90 (s, 2H), 7.30 (m, 3H); $^{13}$C($^1$H) (75 MHz, CD$_3$OD) δ 43.14, 43.24, 45.23, 61.50, 61.86, 62.22, 63.97, 131.92, 133.61, 134.64, 135.10, 136.20, 140.68; MS m/z (M$^+$) 249.

We claim:

1. A water soluble transition metal catalyst having the general formula R$_x$—C—M—L, wherein:

C denotes an indenyl group;

R is an electron withdrawing group selected from the group consisting of a nitrile, ester, ketone, amide, chloro, or fluoro;

X=0, 1 or 2;

M is a transition metal selected from the group consisting of Rh or Ir; and

L is a ligand selected from the group consisting of two separate 2 electron π-ligands or one 4 electron π-ligand of a transition metal.

2. A water soluble transition metal catalyst having the general formula R$_x$—C—M—L, wherein:

C denotes a cyclopentadienyl or indenyl group;

R is an electron withdrawing group selected from the group consisting of a nitrile, ester, ketone, amide, chloro, or fluoro; wherein R also contains a polar functional group selected from the group consisting of an amine, amide, sulfoxide, sulfonate, hydroxyl, guanidinium, polyamine, putracene, or spermadine;

X=0, 1 or 2;

M is a transition metal selected from the group consisting of Co, Rh or Ir; and

L is a ligand selected from the group consisting of two separate 2 electron π-ligands or one 4 electron π-ligand of a transition metal.

3. The water soluble transition metal catalyst of claim 2 wherein L contains one or more functional groups (R$_1$), selected from the group consisting of an amine, sulfonate, hydroxyl, guanidinium, polyamine, putracene, or spermadine.

4. A water soluble transition metal catalyst having the general formula:

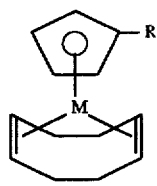

wherein R is an electron withdrawing group selected from the group consisting of a nitrile, ester, ketone, amide, chloro or fluoro; and M is a transition metal selected from the group consisting of Rh or Ir.

5. A water soluble transition metal catalyst having the general formula:

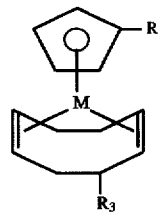

wherein R is an electron withdrawing group selected from the group consisting of a nitrile, ester, ketone, amide, chloro or fluoro; and M is a transition metal selected from the group consisting of Co, Rh or Ir.; and R$_3$ is a polar functional group selected from the group consisting of an amine, sulfonate, hydroxyl, guanidinium, polyamine, putracene, or spermadine.

6. A water soluble transition metal catalyst having the general formula:

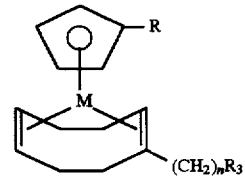

wherein R is an electron withdrawing group selected from the group consisting of a nitrile, ester, ketone, amide, chloro or fluoro; and M is a transition metal selected from the group consisting of Co, Rh or Ir.; and R$_3$ is a polar functional group selected from the group consisting of an amine, sulfonate, hydroxyl, guanidinium, polyamine, putracene, or spermadine; and n=1–8.

7. A water soluble transition metal catalyst having the formula:

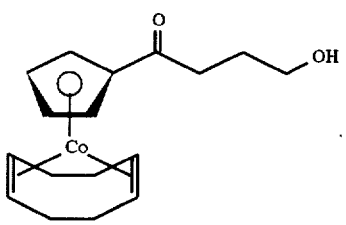

8. A water soluble transition metal catalyst having the formula:

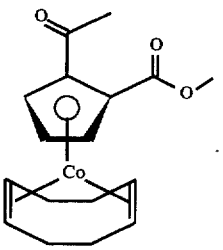

9. A water soluble transition metal catalyst having the general formula $R_x$—Cp—Co—L, wherein:
R is an electron withdrawing group selected from the group consisting of a nitrile, amide, or fluoro;
X=1 or 2; and
L is a ligand selected from the group consisting of two separate 2 electron π-ligands or one 4 electron π-ligand of a transition metal.

10. The water soluble transition metal catalyst of claim 7 wherein L is selected from the group consisting of propenes, butenes, pentenes, cyclopentenes, hexenes, cyclohexenes, cyclobutadiene, cyclohexadiene or cyclooctadiene.

11. A water soluble transition metal catalyst having the general formula:

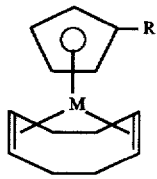

wherein R is an electron withdrawing group selected from the group consisting of a nitrile, amide or fluoro.

12. A water soluble transition metal catalyst having the general formula $R_x$—C—Co—M—L, wherein:
C denotes an indenyl group;
R is an electron withdrawing group selected from the group consisting of a nitrile, ester, ketone, amide, chloro, or fluoro;
X=1 or 2; and
L is a ligand selected from the group consisting of two separate 2 electron π-ligands or one 4 electron π-ligand of a transition metal.

13. A water soluble transition metal catalyst having the general formula $R_x$—C—Co—$L_y$, wherein:
C denotes an indenyl group;
R is an electron withdrawing group selected from the group consisting of a nitrile, ester, ketone, amide, chloro, or fluoro;

X=0, 1 or 2;
L is a ligand selected from the group consisting of ethenes, propenes, butenes, pentenes, cyclopentenes, hexenes, cyclohexenes, cyclobutadiene or cyclohexadiene; and
y=1 or 2.

14. A water soluble transition metal catalyst having the general formula $R_x$—C—Co—L, wherein:
C denotes an indenyl group;
R is an electron withdrawing group selected from the group consisting of a nitrile, ester, ketone, amide, chloro, or fluoro;
X=1 or 2; and
L is cyclooctadiene.

15. A water soluble transition metal catalyst having the general formula $R_x$—Cp—Rh—L, wherein:
R is an electron withdrawing group selected from the group consisting of a nitrile, ester, amide, or fluoro;
X=0, 1 or 2; and
L is a ligand selected from the group consisting of two separate 2 electron π-ligands or one 4 electron π-ligand of a transition metal.

16. A water soluble transition metal catalyst having the general formula $R_x$—Cp—Rh—$L_2$, wherein:
R is an electron withdrawing group selected from the group consisting of a nitrile, ester, ketone, amide, chloro or fluoro;
X=0, 1 or 2; and
L is a ligand selected from the group consisting of propenes, butenes, pentenes, cyclopentenes, hexenes, cyclohexenes, cyclobutadiene, cyclohexadiene or cyclooctadiene; and
y=1 or 2.

17. A water soluble transition metal catalyst having the general formula $R_x$—Cp—Ir—L, wherein:
R is an electron withdrawing group selected from the group consisting of a nitrile, ester, amide, chloro or fluoro;
X=0, 1 or 2; and
L is a ligand selected from the group consisting of two separate 2 electron π-ligands or one 4 electron π-ligand of a transition metal.

18. A water soluble transition metal catalyst having the general formula $R_x$—Cp—Ir—$L_2$, wherein:
R is an electron withdrawing group selected from the group consisting of a nitrile, ester, ketone, amide, chloro or fluoro;
X=0, 1 or 2; and
L is a ligand selected from the group consisting of propenes, butenes, pentenes, cyclopentenes, hexenes, cyclohexenes, cyclobutadiene, cyclohexadiene or cyclooctadiene; and
y=1 or 2.

19. The water soluble transition metal catalyst of claim 1 wherein L is selected from the group consisting of propenes, butenes, pentenes, cyclopentenes, hexenes, cyclohexenes, cyclobutadiene, cyclohexadiene or cyclooctadiene.

* * * * *